(12) United States Patent
Lim et al.

(10) Patent No.: US 7,025,745 B2
(45) Date of Patent: Apr. 11, 2006

(54) METHOD OF MAKING A CATHETER BALLOON USING A TAPERED MANDREL

(75) Inventors: Florencia Lim, Union City, CA (US); Fozan El-Nounou, Santa Clara, CA (US); Alfredo Bayot, Newark, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 642 days.

(21) Appl. No.: 10/266,010

(22) Filed: Oct. 7, 2002

(65) Prior Publication Data

US 2004/0068287 A1   Apr. 8, 2004

(51) Int. Cl.
*A61M 31/00* (2006.01)
*A61M 29/00* (2006.01)
*B29C 49/08* (2006.01)

(52) U.S. Cl. .............. 604/103.06; 606/194; 264/288.4

(58) Field of Classification Search ............ 604/96.01, 604/103.06, 103.07, 103.08, 103.09; 606/194; 264/632, 209.1, 209.5, 209.3, 210.1, 167, 264/288.4
See application file for complete search history.

(56) References Cited

U.S. PATENT DOCUMENTS

| | | | |
|---|---|---|---|
| 5,273,536 A * | 12/1993 | Savas | ............... 604/103.07 |
| 5,334,146 A * | 8/1994 | Ozasa | ................ 604/103.06 |
| 5,338,298 A * | 8/1994 | McIntyre | ............... 604/103.07 |
| 5,868,704 A | 2/1999 | Campbell et al. | |
| 6,016,848 A | 1/2000 | Egres, Jr. | |
| 6,120,477 A | 9/2000 | Campbell et al. | |
| 6,203,735 B1 | 3/2001 | Edwin et al. | |
| 6,277,139 B1 | 8/2001 | Levinson et al. | |
| 6,375,637 B1 | 4/2002 | Campbell et al. | |
| 6,428,506 B1 | 8/2002 | Simhambhatla et al. | |
| 6,436,135 B1 | 8/2002 | Goldfarb | |

FOREIGN PATENT DOCUMENTS

| | | |
|---|---|---|
| WO | WO 95/05555 | 2/1995 |
| WO | WO 97/02791 | 1/1997 |

* cited by examiner

*Primary Examiner*—Sharon Kennedy
(74) *Attorney, Agent, or Firm*—Fulwider Patton LLP (57) ABSTRACT

A method of making a catheter balloon, and a balloon catheter formed thereby, in which a layer of a catheter balloon is formed by decreasing the inner diameter of a first end section of a polymeric tube, so that the tube has a reduced diameter first end section with an inner diameter less than the inner diameter of a central section of the tube. The reduced diameter first end section of the tube is bonded to a catheter shaft to form at least a portion of a skirt section of the balloon, and the skirt section has an improved high rupture pressure.

17 Claims, 4 Drawing Sheets

METHOD OF MAKING A CATHETER BALLOON USING A TAPERED MANDREL

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

Catheter balloons formed of expanded polytetrafluoroethylene (ePTFE) expanded in place within the patient's body lumen without blow molding the ePTFE tubing have been disclosed. Prior disclosed methods of forming an ePTFE balloon involved wrapping a sheet of ePTFE on a mandrel and heating the wrapped sheet to fuse the layers of wrapped material together to form a tube. The resulting ePTFE tube may be subsequently heated in one or more additional heating steps and otherwise further processed, and combined with a nonporous liner to complete formation of the balloon. However, one difficulty has been the failure of the bonds between the balloon and the catheter shaft during inflation of the balloon at the relatively high inflation pressures required in angioplasty or stent delivery. Thus, it would be a significant advance to provide a balloon catheter having strong, durable bonds between the balloon and the shaft.

SUMMARY OF THE INVENTION

This invention is directed to a method of making a catheter balloon, and a balloon catheter formed thereby, in which a layer of a catheter balloon is formed by decreasing the inner diameter of a first end section of a polymeric tube, so that the tube has a reduced diameter first end section with an inner diameter less than the inner diameter of a central section of the tube. The reduced diameter first end section of the tube is bonded to a catheter shaft to form at least a portion of a skirt section of the balloon, providing a skirt section with an improved high rupture pressure.

The method of making a catheter balloon of the invention generally comprises providing a polymeric tube having a central section and a first end section with an inner diameter, and decreasing the inner diameter of the first end section of the polymeric tube to form a reduced diameter first end section. In one embodiment, the reduced diameter first end section has at least a portion having an inner diameter about 10% to about 45% less than an inner diameter of the central section of the tube.

In a presently preferred embodiment, the inner diameter of the first end section of the polymeric tube is decreased by longitudinally stretching the tube onto an outer surface of a mandrel. The outer surface of the mandrel transitions from a first outer diameter to a second smaller outer diameter. The stretched tube is preferably heated on the mandrel in the stretched configuration to stabilize the tube in the stretched configuration, and the stretched tube may be further processed after heating, and attached to a catheter shaft to form a layer of a catheter balloon having at least one layer.

A balloon which embodies features of the invention can be used on a variety of suitable balloon catheters including coronary and peripheral dilatation catheters, stent delivery catheters, drug delivery catheters and the like. The balloon catheter of the invention generally comprises an elongated shaft having at least one lumen, and the balloon secured to a distal shaft section so that the balloon has an interior in fluid communication with the shaft lumen for delivery of inflation media to the balloon interior. The balloon typically has a proximal skirt section bonded to a first portion of the shaft, a distal skirt section bonded to a second portion of the shaft, and an inflatable section therebetween. The balloon is bonded to the shaft by a variety of suitable methods including fusion bonding and adhesive bonding. The reduced diameter end section of the porous polymeric tube preferably forms at least a portion of the distal skirt section of the balloon. Although discussed below primarily in terms of the embodiment in which the reduced diameter distal end section forms at least a portion of the distal skirt section, it should be understood that in an alternative embodiment the balloon has a proximal skirt section formed at least in part by a reduced diameter proximal end section of the polymeric tube forming a layer of the balloon. For example, in one embodiment, the balloon has a polymeric layer with a reduced diameter distal end section forming at least a portion of the distal skirt section of the balloon, and with a reduced diameter proximal end section forming at least a portion of the proximal skirt section of the balloon, both reduced diameter end sections being formed according to the method of the invention.

The reduced diameter distal end section of the polymeric tube forms a balloon distal skirt section with an improved strong bond to the catheter shaft. The high rupture pressure of the distal skirt section of the balloon allows the balloon to be inflated at relatively high inflation pressures. Moreover, the reduced diameter section has a reduced wall thickness which provides a low profile skirt section. Additionally, the reduced wall thickness of the distal skirt section reduces the disadvantageously high stiffness which is otherwise present at balloon skirt sections. In one embodiment, the reduced diameter distal end section tapers throughout all or a substantial portion of the length thereof, which further improves the stiffness transition of the distal skirt section.

In a presently preferred embodiment, the polymeric material of the polymeric tube forming a layer of the catheter balloon comprises a polymer having a porous structure, which in one embodiment is selected from the group consisting of expanded polytetrafluoroethylene (ePTFE), an ultra high molecular weight polyolefin such as ultra high molecular weight polyethylene, and porous polyolefins such as polyethylene and polypropylene, and porous polyurethane. In one embodiment, the porous material has a node and fibril microstructure. The node and fibril microstructure, when present, is produced in the material using conventional methods. For example, ePTFE and ultra high molecular weight polyethylene (also referred to as "expanded ultra high molecular weight polyethylene") typically have a node and fibril microstructure, and are not melt extrudable. However, a variety of suitable polymeric materials can be used in the method of the invention, including conventional catheter balloon materials which are melt extrudable. In one presently preferred embodiment, the polymeric material cannot be formed into a balloon by conventional balloon blow molding, and is formed into a balloon by heat fusing wrapped layers of the polymeric material together to form a tubular member. Porous materials such as ePTFE and ultrahigh molecular weight polyethylene typically require a nonporous second layer or liner when used to form an inflatable balloon. Thus, the balloon layer formed according to the method of the invention is a layer of a balloon having at least one layer, and in one embodiment, is a layer of a multilayered balloon having a nonporous second layer. In a presently preferred embodiment having the nonporous second layer, a second polymer tube which forms the nonporous second layer (and which is preferably formed of an elastomeric polymer) is positioned in at least the central section of the porous polymeric tube before the reduced inner diameter end section of the porous polymeric tube is bonded to the shaft. The elastomeric polymer layer is typically an inner layer, and has proximal and distal end sections bonded to the shaft. The elastomeric polymer tube is preferably bonded to the shaft during the bonding of the porous polymeric tube to the shaft, although it may alternatively be bonded to the shaft before the porous polymeric tube.

In one embodiment, the entire length of the reduced diameter end section of the porous polymeric tube is bonded directly to the shaft. Alternatively, some or all of the length of the reduced diameter end section of the porous polymeric tube is bonded to an underlying section of the elastomeric polymer tube which is bonded to the shaft. The porous polymeric tube is typically longitudinally compacted before being secured to the balloon second layer, and the second (e.g., elastomeric) layer is typically not longitudinally compacted. Longitudinal compaction of the porous polymeric tube decreases the length of the section and preferably also decreases the porosity of the material forming the section.

The invention provides a balloon catheter having a balloon secured to the shaft by an improved strong bond, providing an improved increased rupture pressure at the bond between the balloon skirt section and the shaft. Moreover, the method provides a balloon having a low profile skirt section with an improved flexibility transition along the length thereof. These and other advantages of the invention will become more apparent from the following detailed description of the invention and the accompanying exemplary drawings.

DETAILED DESCRIPTION OF THE INVENTION

Figure 1:
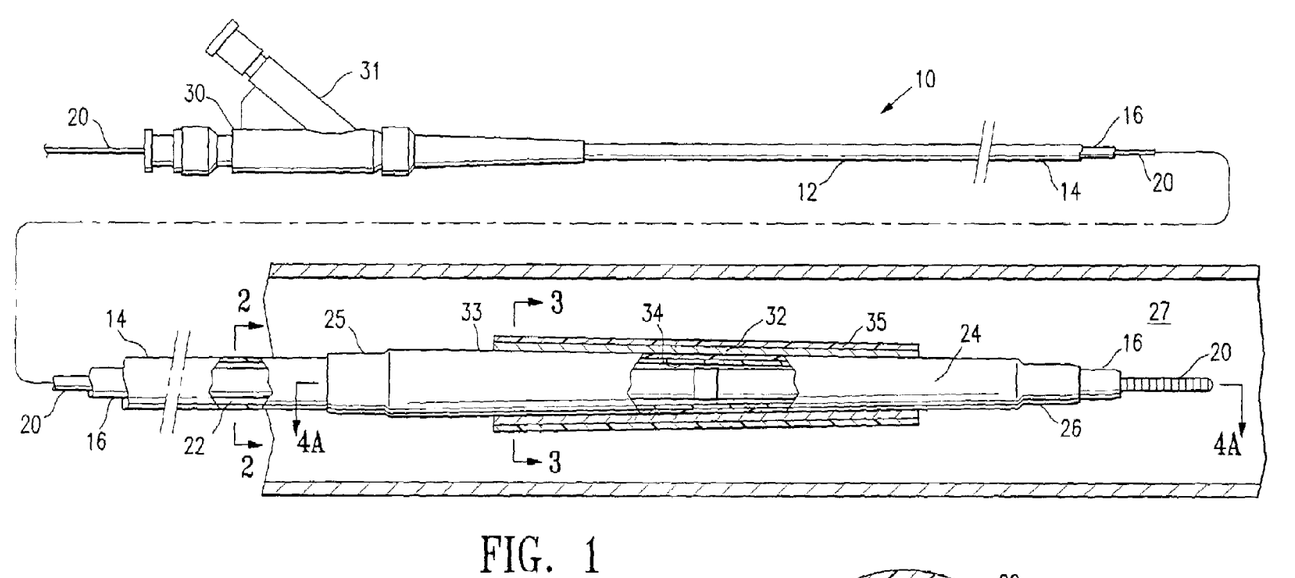
FIG. 1 is an elevational view, partially in section, of a stent delivery balloon catheter embodying features of the invention.
Figure 2:
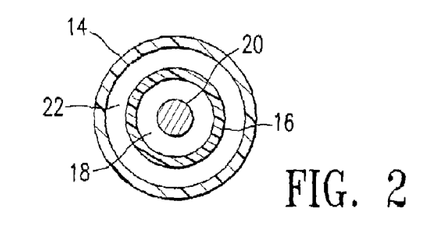
FIG. 2 is a transverse cross sectional view of the balloon catheter shown in FIG. 1, taken along line 2—2.
Figure 3:
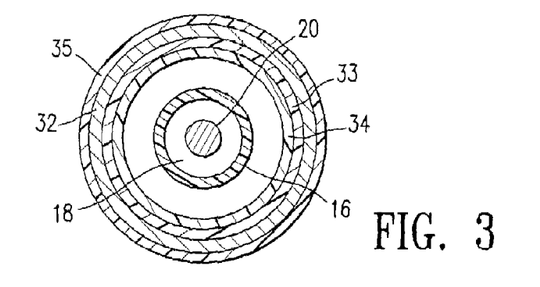
FIG. 3 is a transverse cross sectional view of the balloon catheter shown in FIG. 1, taken along line 3—3.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. FIG. 1 illustrates the balloon 24 in a low profile tubular configuration prior to complete inflation, with an expandable stent 32, with a stent cover 35 thereon, mounted on the balloon for delivery within a patient's body lumen 27. The distal end of the catheter may be advanced to a desired region of the body lumen 27 in a conventional manner, and balloon 24 inflated to expand covered stent 32, and the balloon deflated, leaving covered stent 32 implanted in the body lumen 27.

In the embodiment illustrated in FIG. 1, balloon 24 has a first layer 33 and a second layer 34. In a presently preferred embodiment, the balloon 24 first layer 33 comprises a microporous polymeric material, and preferably a microporous polymeric material having a node and fibril microstructure, such as ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that the first layer may comprise other materials, including ultrahigh molecular weight polyethylene. The second layer 34 is preferably formed of an elastomeric material, such as polyurethane elastomers, silicone rubbers, styrene-butadiene-styrene block copolymers, polyamide block copolymers, and the like. In a preferred embodiment, layer 34 is an inner layer relative to layer 33, although in other embodiments it may be an outer layer. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer.

Figure 4A:
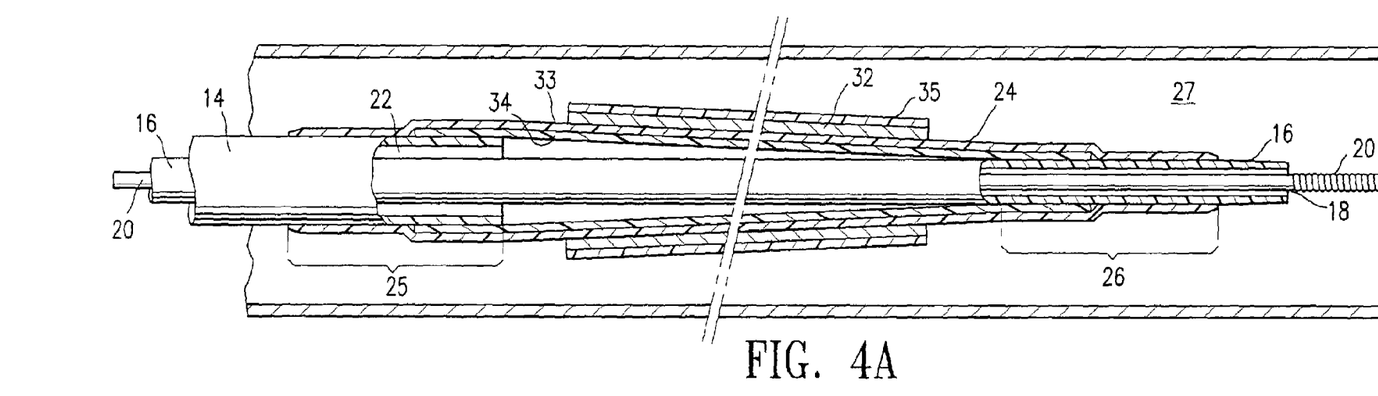
FIG. 4A is an enlarged longitudinal cross section of the balloon catheter of FIG. 1, taken along line 4A—4A.
Figure 4B:
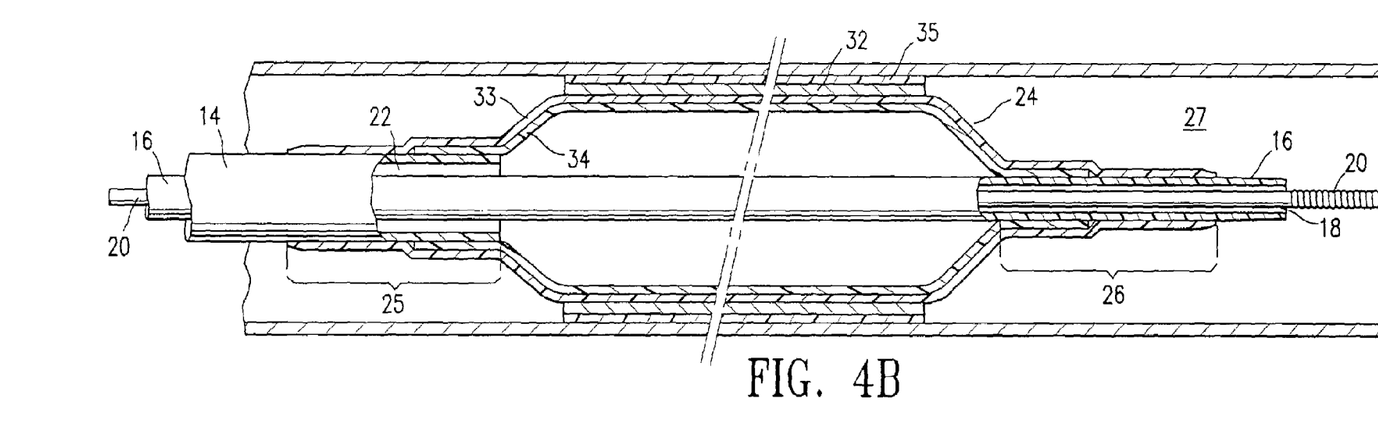
FIG. 4B illustrates the balloon catheter of FIG. 4A, with the balloon inflated.

FIG. 4A is an enlarged, longitudinal cross section of the balloon catheter 10 of FIG. 1, taken along line 4A—4A. FIG. 4B illustrates the balloon catheter of FIG. 4A with the balloon in an inflated configuration. The inflated balloon 24 has a central working section with stent 32 mounted thereon, a proximal tapered section between the working section and the proximal skirt section 25, and a distal tapered section between the distal skirt section 26 and the working section. The section of the first layer 33 extending along the working section of the balloon is hereafter referred to as the first layer working section. Similarly, the first layer proximal and distal tapered sections refer to the sections of the first layer 33 extending along the proximal and distal tapered sections of the balloon, and the first layer skirt sections refer to the sections of the first layer 33 extending along the balloon skirt sections 25, 26. Although the balloon 24 is illustrated in FIG. 4B with a conventional inflated configuration having a central working length between two tapered inflatable sections, it should be understood that the inflated balloon may have a variety of suitable configurations including balloon configurations specially shaped for a particular anatomy such as a focal balloon configuration, a conical balloon configuration, and the like, as are conventionally known to one of skill in the art.

The first and second layers 33, 34 of balloon 24 each extend from the proximal skirt section 25 of the balloon to the distal skirt section 26 of the balloon. The first layer 33 can have a length which is the same as or shorter than the length of the second layer 34, or alternatively, can have end sections which extend beyond the end sections of the second layer 34 and onto the shaft. The skirt sections 25, 26 of the balloon typically comprise end sections of the second (inner) layer 34 having an inner surface bonded to the shaft, and sections of the first (outer) layer 33 having an inner surface bonded to the end sections of the second layer 34 which are bonded to the shaft. In the embodiment of FIG. 4, the skirt sections 25, 26 are also formed in part by end sections of the first layer 33 which extend beyond the end sections of the second layer 34 and which are bonded directly to the shaft without the second layer 34 or another member therebetween. The terminology "directly bonded" should be understood to include a variety of bonding methods including fusion and adhesive bonding.

Figure 5:
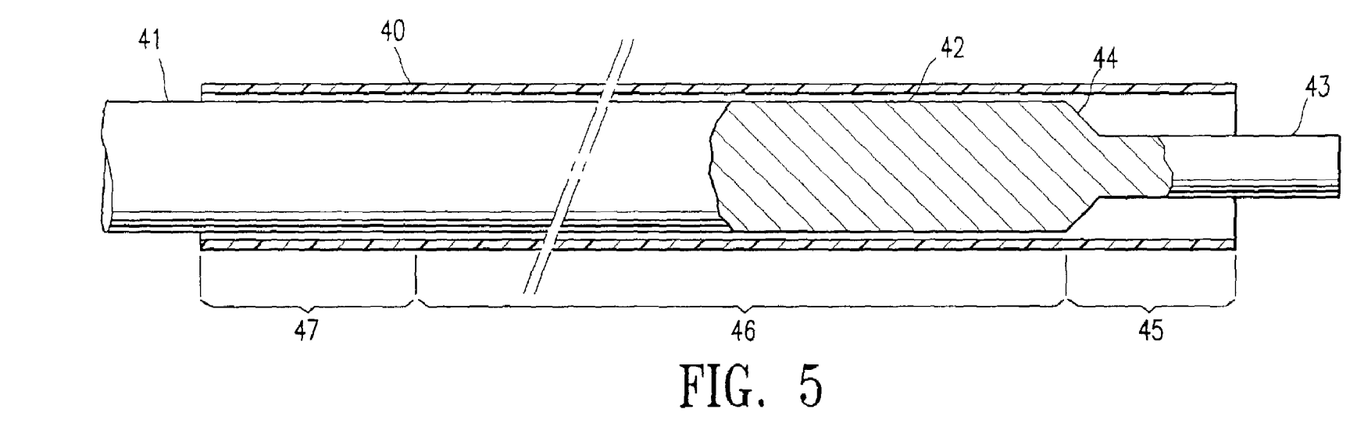
FIG. 5 illustrates an assembly of a tube of porous polymeric material on a mandrel before the tube is longitudinally stretched onto the outer surface of the mandrel which transitions from a first outer diameter to a second small outer diameter.
Figure 6:
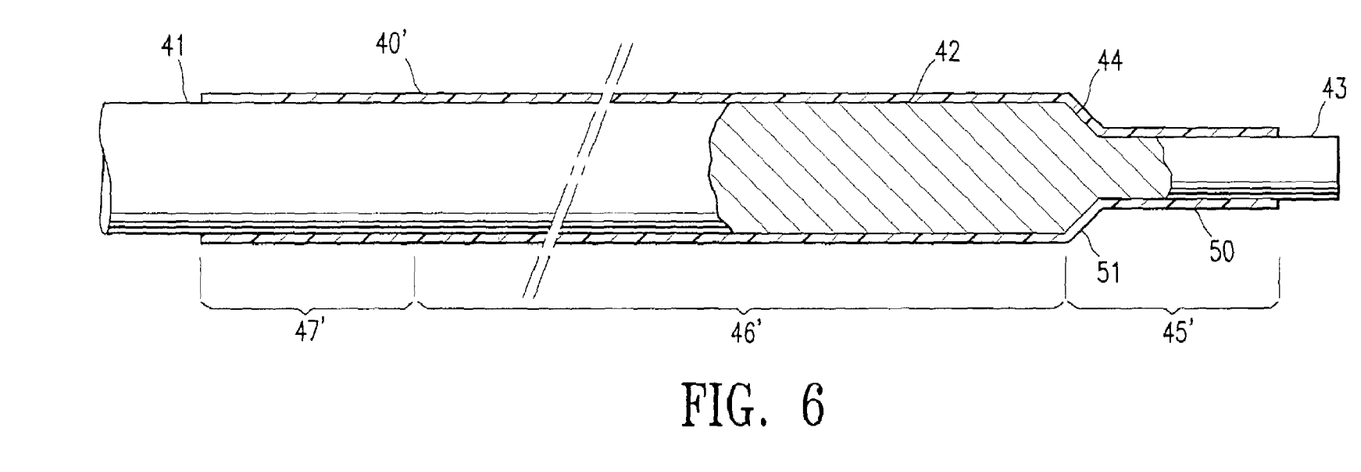
FIG. 6 illustrates the assembly of FIG. 5, after the porous polymeric tube is longitudinally stretched onto the mandrel surface to decrease the inner diameter of the distal end section of the tube.

FIGS. 5 and 6 illustrate an assembly of a porous polymeric tube 40 on a mandrel 41, during formation of a layer of a catheter balloon in a method which embodies features of the invention. The polymeric material of the tube 40 is ePTFE in the embodiment in which the tube forms ePTFE layer 33 of the balloon 24 of FIG. 1. The mandrel 41 has a first section 42 with a first outer diameter, and a second section 43 with a second smaller outer diameter. A tapered section 44 tapers from the first section 42 to the second section 43. The mandrel can have a variety of suitable configurations forming a transition from a first outer diameter to a second smaller outer diameter. For example, although the mandrel second section 43 has a uniform diameter in the illustrated embodiment, in an alternative embodiment (not shown), the second section 43 has a tapered outer diameter either with or without tapered section 44 being present.

FIG. 5 illustrates the ePTFE tube 40 around the mandrel 41 before the tube is longitudinally stretched onto the mandrel. The ePTFE tube 40 has a distal end section 45 overlying the second section 43 and the tapered section 44 of the mandrel 41, and a central section 46 overlying the first section 42 of the mandrel 41. A proximal end section 47 of the tube 40 is at the proximal end of the central section 46. The first section 42 of mandrel 41 has an outer diameter which is preferably not significantly smaller than the inner diameter of the central section 46 of the ePTFE tube 40. The outer diameter of the mandrel first section 42 is typically about 0.7 to about 1 mm, and the second section 43 outer diameter is typically about 0.5 to about 0.7 mm.

The ePTFE tube 40 is longitudinally stretched, as for example by being pulled at either end, to stretch it down on to the mandrel. The tube 40 may be at an elevated temperature during stretching, or alternatively at ambient (i.e., room) temperature. FIG. 6 illustrates the ePTFE tube 40 of FIG. 5 after being longitudinally stretched onto the surface of the mandrel 41 to form longitudinally stretched tube 40'. The stretched tube 40' has a reduced diameter distal end section 45' on sections 43 and 44 of the mandrel 41, and central section 46' and proximal end section 47' on the first section 42 of the mandrel.

In the illustrated embodiment, the reduced diameter distal end section 45' of the stretched tube 40' has a uniform diameter portion 50 and a tapered portion 51 tapering distally away from the central section 46' to the uniform diameter portion 50. The uniform diameter portion 50 has an inner diameter about 10 to about 45%, preferably about 15 to about 35% less than the inner diameter of the central section 46' of stretched tube 40'. Specifically, in one embodiment, the uniform diameter portion 50 inner diameter is about 0.4 to about 0.8 mm, preferably about 0.5 to about 0.7 mm, and the central section 46' inner diameter is about 0.6 to about 1 mm, preferably about 0.7 to about 0.9 mm. The tapered portion 51 typically tapers at an angle of about 15 to about 90 degrees, preferably about 30 to about 80 degrees, and has a length of about 0.5 to about 6 mm, preferably about 1 to about 3 mm. The uniform diameter portion 50 has a length of about 1 to about 6 mm, preferably about 2 to about 4 mm, and the central section 46' has a length of about 8 to about 60 mm.

During the longitudinal stretching of the ePTFE tube 40 onto mandrel 41, the inner diameter of the ePTFE tube 40 at distal end section 45 decreases by about 60% to about 90%, more specifically by about 70% to about 80%, to form reduced diameter distal end section 45' (of longitudinally stretched tube 40'). The inner diameter of the ePTFE tube 40 at the central section 46 decreases a smaller amount, and specifically about 50% to about 85%, more specifically about 60% to about 75%, to form central section 46' (of longitudinally stretched tube 40') during the longitudinal stretching of the ePTFE tube 40 onto mandrel 41. Although the wall thickness of the stretched tube 40' is illustrated as being the same as the wall thickness of the tube 40 for ease of illustration, it should be understood that the tube 40' along at least the reduced diameter distal end section 45' typically has a reduced wall thickness as a result of the process of stretching the tube 40 down onto the mandrel 43.

The longitudinally stretched tube 40' is preferably heated on the mandrel 41 in the stretched configuration to stabilize the tube 40' in the stretched configuration. The tube 40' is typically heated at an elevated temperature of about 320° C. to about 400° C., and specifically in the embodiment in which tube 40' is ePTFE, at an elevated temperature of about 350° C. to about 380° C.

After being longitudinally stretched and before bonding to the shaft, the tube 40' is preferably longitudinally compacted, optionally while still on mandrel 41. After being longitudinally compacted, the tube 40' may be heat treated or otherwise further processed before being secured to the second layer 34 and to the shaft 12 to form balloon 24.

Figure 7:
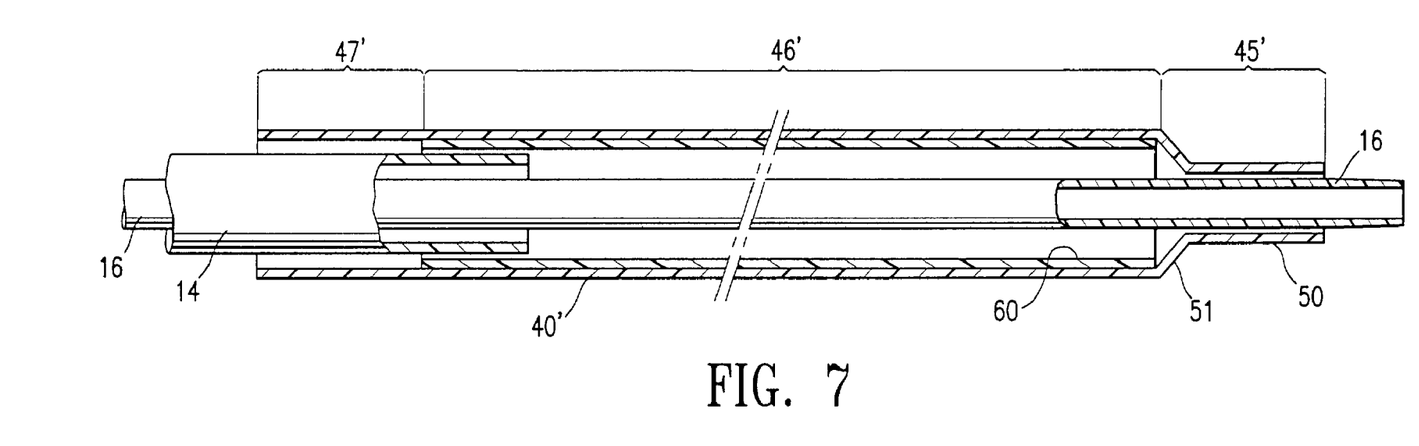
FIG. 7 illustrates the porous polymeric tube of FIG. 5, positioned around a catheter shaft and with an elastomeric polymer layer in a central section of the tube, prior to bonding to the catheter shaft.
Figure 8:
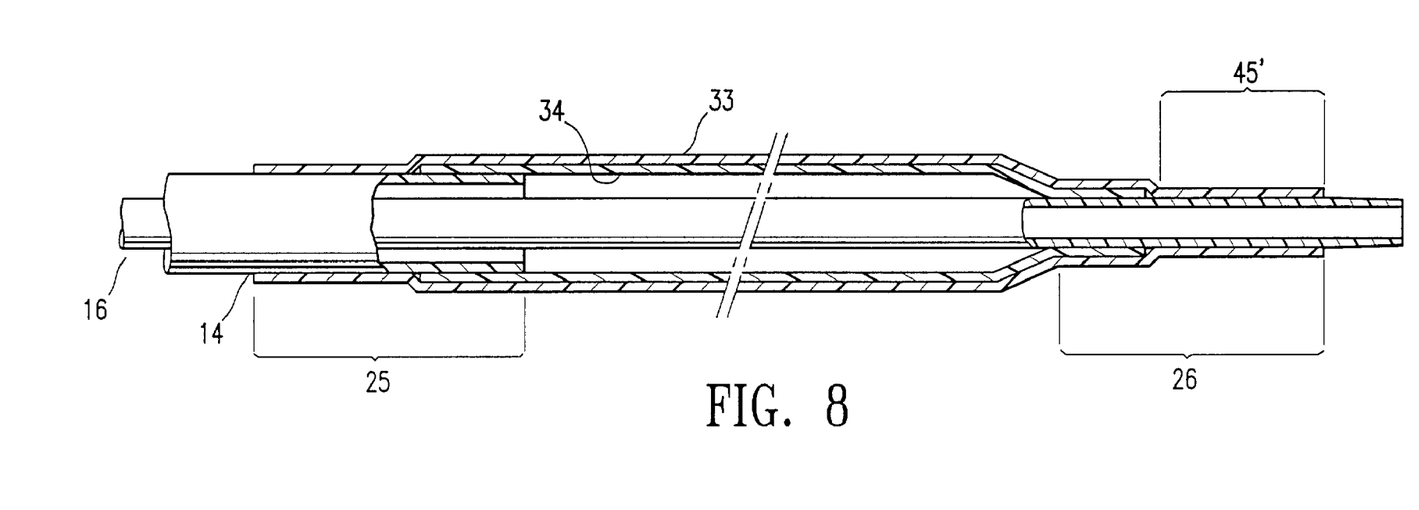
FIG. 8 illustrates the porous polymeric tube and elastomeric polymer layer of FIG. 7, after bonding to the catheter shaft.

FIG. 7 illustrates the tube 40' positioned around the shaft 11 outer tubular member 14 and inner tubular member 16. An elastomeric tube 60 which forms second/inner layer 34 of balloon 24 is positioned in the central section 46' of the tube 40'. The distal end of the elastomeric tube 60 is at the distal end of the central section 46' of the tube 40'. Portion 50 of the reduced diameter distal end section 45' of the tube 40' has an inner diameter about 0% to about 30%, more specifically about 1% to about 18% greater than an outer diameter of the inner tubular member 16, so that the gap (if any) between the tube 40' and the inner tubular member 16 is smaller than it otherwise would be (i.e., the gap is smaller than would be present if the inner diameter of the distal end section of the tube 40 had not been reduced to form reduced diameter section 45'). In embodiments in which the inner diameter of the reduced diameter distal end section 45' is not greater than the outer diameter of the inner tubular member 16, the distal end of the section 45' is typically flared or otherwise opened up to allow the section 45' to be placed around the inner tubular member 16 for bonding thereto. The reduced diameter distal end section 45' is bonded to the shaft, thereby forming part of the distal skirt section 26 of the balloon 24. Specifically, in a presently preferred embodiment, a heating nozzle traverses a portion of the tube 40' to be bonded to the inner tubular member, optionally with heat shrink tubing around the tube portion to heat and bond the tube 40' onto the inner tubular member 16. In a presently preferred embodiment, the portion of the tube 40' which is bonded to the inner tubular member 16 extends from a distal portion of the central section 46' having elastomeric tube 60 therein, and along the reduced diameter distal end section 45'. Thus, a distal portion of central section 46' of tube 40' with an underlying portion of the elastomeric tube 60 bonds to the inner tubular member 16, while the uniform diameter portion 50 and tapered portion 51 extending distally of the elastomeric tube 60 are bonded directly to the inner tubular member 16. FIG. 8 illustrates the tube 40' of FIG. 7, after bonding to the inner tubular member 16 and outer tubular member 14. The reduced diameter distal end section 45' (made up of the uniform diameter portion 50 and tapered portion 51) of tube 40' form the part of the ePTFE tube 40' bonded directly to the shaft, to form a distal portion of the distal skirt section 26 of the balloon 24. The balloon is shown partially inflated in FIG. 8

Balloon 24 of catheter 10, formed according to a method embodying features of the invention, preferably has a distal skirt section 26 with a rupture pressure of about 14 atm (210 psi) to about 28 atm (410 psi) depending on the desired working pressure of the balloon 24. In the embodiment in which balloon 24 is a relatively high pressure balloon (i.e., rated to about 18 atm or above), the distal skirt section 26 preferably has a rupture pressure of not less than about 22 atm (320 psi). Similarly, a proximal skirt section formed according to the method of the invention with a first layer reduced diameter end section would have rupture pressure similar to the distal skirt section, and generally of not less than 20 atm. The longitudinal stretching decreases the wall thickness of the tube, so that the reduced diameter distal end section 45' has a smaller wall thickness than the central section 46' of the tube 40', at least prior to inflation of the balloon 24. Thus, the distal portion of the distal skirt section 26 (defined by the uniform diameter portion 50 and tapered portion 51 of tube 40') bonded directly to shaft has a low profile. The wall thickness of the distal portion of the distal skirt section 26 is typically about 0.07 to about 0.2 mm, and the wall thickness of central section 46' of the tube 40' is about 0.1 to about 0.25 mm.

To the extent not previously discussed herein, the various catheter components may be formed and joined by conventional materials and methods. For example, the outer and inner tubular members can be formed by conventional techniques, such as by extruding and necking materials found useful in intravascular catheters such as polyethylene, polyvinyl chloride, polyesters, polyamides, polyimides, polyurethanes, and composite materials.

The length of the balloon catheter 10 is generally about 108 to about 200 centimeters, preferably about 137 to about 145 centimeters, and typically about 140 centimeters for PTCA. The outer tubular member 14 has an outer diameter (OD) of about 0.017 to about 0.036 inch (0.43–0.91 mm), and an inner diameter (ID) of about 0.012 to about 0.035 inch (0.30–0.89 mm). The inner tubular member 16 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 24 has a length of about 8 mm to about 80 mm, typically about 8 mm to about 38 mm, and an inflated working diameter of about 1.5 mm to about 20 mm, typically about 2 mm to about 10 mm.

While the present invention has been described herein in terms of certain preferred embodiments, those skilled in the art will recognize that modifications and improvements may be made without departing from the scope of the invention. For example, although the embodiment illustrated in FIG. 1 is an over-the-wire stent delivery catheter, balloons of this invention may also be used with other types of intravascular catheters, such as rapid exchange balloon catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. Additionally, although not illustrated, a soft distal tip member may be provided at the distal end of the catheter, and bonded to the balloon distal skirt section 26, as is conventionally known. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A method of making a balloon catheter, comprising:
   a) providing a porous polymeric tube having a central section and a first end section with an inner diameter, and decreasing the inner diameter of the first end section of the porous polymeric tube to form a reduced diameter first end section at least a portion thereof having an inner diameter less than an inner diameter of the central section of the tube, to form a layer of a catheter balloon having at least one layer; and
   b) attaching the catheter balloon to a catheter shaft by bonding the reduced diameter first end section of the porous polymeric tube to the shaft, and bonding a second end section of the porous polymeric tube to the shaft, to form a balloon catheter having the balloon bonded to the shaft at proximal and distal skirt sections of the balloon.

2. The method of claim 1 wherein decreasing the diameter of the first end section comprises longitudinally stretching the tube to decrease the diameter of an end portion of the first end section to an inner diameter which is about 10 to about 45% less than the inner diameter of the central section of the tube.

3. The method of claim 1 including after a) and before the reduced diameter first end section is bonded to the shaft, positioning an elastomeric polymer tube in the porous polymeric tube extending along at least the central section of the porous polymeric tube.

4. The method of claim 3 wherein the elastomeric polymer tube is extending along only the central section of the porous polymeric tube and is not extending along the reduced diameter first end section of the porous polymeric tube, and attaching the balloon to the shaft further includes bonding a portion of the central section of the porous polymeric tube with an underlying portion of the elastomeric polymer tube to the shaft.

5. The method of claim 1 wherein the reduced diameter first end section comprises a tapered portion tapering away from the central section to a uniform diameter portion.

6. The method of claim 1 wherein decreasing the inner diameter of the first end section comprises longitudinally stretching the tube onto a mandrel having an outer surface which transitions from a first outer diameter to a second smaller outer diameter, and heating the tube in the stretched configuration on the mandrel.

7. The method of claim 6 wherein the porous polymeric material is selected from the group consisting of expanded polytetrafluoroethylene, ultra high molecular weight polyolefin, porous polyolefin, and porous polyurethane, and the stretched tube is heated at an elevated temperature of about 320 to about 400° C. to stabilize the tube in the stretched configuration.

8. A method of making a balloon catheter, comprising:
   a) longitudinally stretching a porous polymeric tube onto an outer surface of a mandrel which transitions from a first outer diameter to a second smaller outer diameter, and heating the stretched tube on the mandrel in the stretched configuration, to form a layer of a catheter balloon having at least one layer, the layer having a proximal end section, a central section with a first inner diameter, and a reduced diameter distal end section with a second inner diameter less than the first inner diameter; and
   b) attaching the balloon to a catheter shaft having at least one lumen so that the balloon has an interior in fluid communication with the shaft lumen, by bonding the reduced diameter distal end section of the porous polymeric layer to a first portion of the catheter shaft, and bonding the proximal end section of the porous polymeric layer to a second portion of the catheter shaft, to form a balloon catheter having a balloon bonded to the shaft at proximal and distal skirt sections of the balloon.

9. The method of claim 7 wherein reduced diameter distal end section of the porous polymeric layer has at least a portion with an inner diameter about 1% to about 30% greater than an outer diameter of the first section of the catheter shaft, and the layer is heated to fusion or adhesively bond the reduced diameter distal end section of the layer to the shaft.

10. The method of claim 7 wherein the reduced diameter distal end section of the layer comprises a tapered portion tapering distally from the central section to a uniform diameter portion having an inner diameter about 10 to about 45% less than the inner diameter of the central section, and bonding the reduced diameter distal end section of the layer to the shaft comprises heating shrink tubing around the tapered portion and the uniform diameter portion of the layer to fusion bond the tapered portion and the uniform diameter portion of the layer to the shaft.

11. The method of claim 7 including after a) and before the reduced diameter distal end section is bonded to the shaft, positioning an elastomeric polymer tube forming an inner layer of the balloon in at least the central section of the porous polymeric layer.

12. The method of claim 10 wherein the elastomeric polymer tube is positioned only in the central section of the porous polymeric layer and is not in the reduced diameter distal end section of the layer, and attaching the balloon to the shaft includes bonding a portion of the central section of the porous polymeric layer with an underlying portion of the elastomeric polymer tube to the shaft.

13. The method of claim 7 wherein the balloon has an inner layer formed of an elastomeric material, and the porous polymeric layer of the balloon is bonded to a section of the balloon inner layer which is bonded to the shaft.

14. The method of claim 7 including longitudinally compacting the stretched tube on the mandrel before b).

15. The method of claim 7 wherein the first inner diameter of the central section of the porous polymeric layer is about 0.03 to about 0.04 inches and the second inner diameter of the reduced diameter distal end section of the layer is about 0.02 to about 0.028 inches, and bonding the layer to the shaft comprises heating the layer to fusion or adhesively bonding the reduced diameter distal end section of the layer to the shaft.

16. The method of claim 14 wherein the shaft comprises an outer tubular member defining the at least one lumen of the shaft, and an inner tubular member disposed in the outer tubular member lumen and defining a guidewire lumen, and the first portion of the shaft bonded to the reduced diameter distal end section of the layer is a portion of the inner tubular member having an outer diameter of about 0.02 to about 0.024 inches, and the second portion of the shaft bonded to the proximal end section of the layer is a distal end of the outer tubular member, so that the balloon has an interior in fluid communication with the outer tubular member lumen.

17. The method of claim 7 wherein the porous polymeric material is selected from the group consisting of expanded polytetrafluoroethylene, ultra high molecular weight polyolefin, porous polyolefin, and porous polyurethane, and the stretched tube is heated at an elevated temperature of about 320 to about 400° C. to stabilize the tube in the stretched configuration.

* * * * *